United States Patent [19]

Morganelli et al.

[11] Patent Number: 5,077,216
[45] Date of Patent: Dec. 31, 1991

[54] MONOCLONAL ANTIBODIES SPECIFIC FOR A HUMAN MONONCULEAR PHAGOCYTE-SPECIFIC ANTIGEN

[75] Inventors: Peter M. Morganelli, West Lebanon; Paul M. Guyre, Hanover, both of N.H.

[73] Assignee: The Trustees of Dartmouth College, Hanover, N.H.

[21] Appl. No.: 215,612

[22] Filed: Jul. 6, 1988

[51] Int. Cl.$^5$ .................. C12N 5/20; C07K 15/28; C12P 21/08
[52] U.S. Cl. .................. 435/240.27; 530/387; 530/388; 435/70.21; 435/172.2
[58] Field of Search .................. 530/387; 435/240.27; 935/108–110

[56] References Cited

U.S. PATENT DOCUMENTS 4,701,408 10/1987 Koestler.

OTHER PUBLICATIONS

Griffin et al., "Expression of Myeloid Differentation Antigens on Normal and Malignant Myeloid Cells", *J. Clin. Invest.*, 68, 932–941, (1981).
Talle, et al., "Patterns of Antigenic Expression on Human Monocytes as Defined by Monoclonal Antibodies", *Cell. Immunol.*, 78, 83–99 (1983).
Sanchez-Madrid et al., "A Human Leukocyte Differentiation Antigen Family with Distinct a–Subunits and a Common b–Subunit", *J. Exp Med.*, 158, 1785–1803, (1983).
Lanier et al., "p150/95, Third member of the LFA–1/CR$_3$ polypeptide family identified by anti–Leu M5 monoclonal antibody", *Eur. J. Immunol.*, 15, 713–718, (1985).
Look et al., "Transfer and Expression of the Gene Encoding a Human Myeloid Membrane Antigen (gp150)," *J. Clin. Invest*, 75: 569–579 (1985).
Schwarting et al., "The Monoclonal Antibodies aS–HCL 1 (aLeu–14) and aS–HCL 3 (aLeu–M5) Allow the Diagnosis of Hairy Cell Leukemia", *Blood*, 65(4), 974–983 (1985).
Takaishi et al., "Monoclonal Antibodies Against Human Myelomonocytic Cells: Detection of Certain Lineage-Specific Antigens on CFU–GM Progenitor Cells", *J. Immunol.*, 135(2), 1523–1529 (1985).
Goyert et al., "Biochemistry and Expression of Myelomonocytic Antigens", *J. Immunol.*, 137(12): 3909–3914 (1986).
Hynes, "Integrins: A Family of Cell Surface Receptors", *Cell*, 48:549–554 (1987).
Hogg et al., Ciba Foundation Symposium 118 (Biochem Macrophage) pp. 68–80, 1986.

*Primary Examiner*—Esther Kepplinger
*Assistant Examiner*—Paula Hutzell
*Attorney, Agent, or Firm*—Lahive & Cockfield

[57] ABSTRACT

A 155 kDa phagocyte-specific antigen which is expressed on human monocytes, monocyte-derived macrophages and peritoneal macrophages, but is not expressed on human granulocytes, lymphocytes and platelets is described.

4 Claims, 7 Drawing Sheets

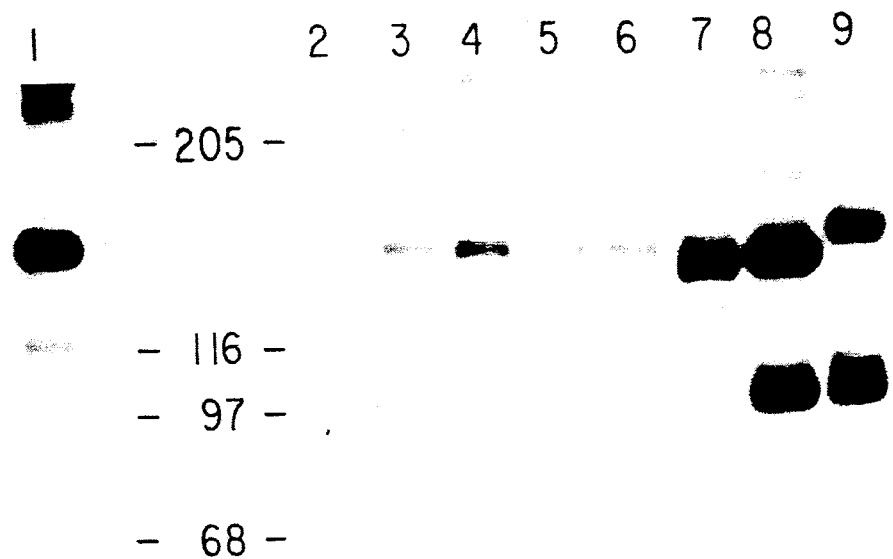
FIG. 8
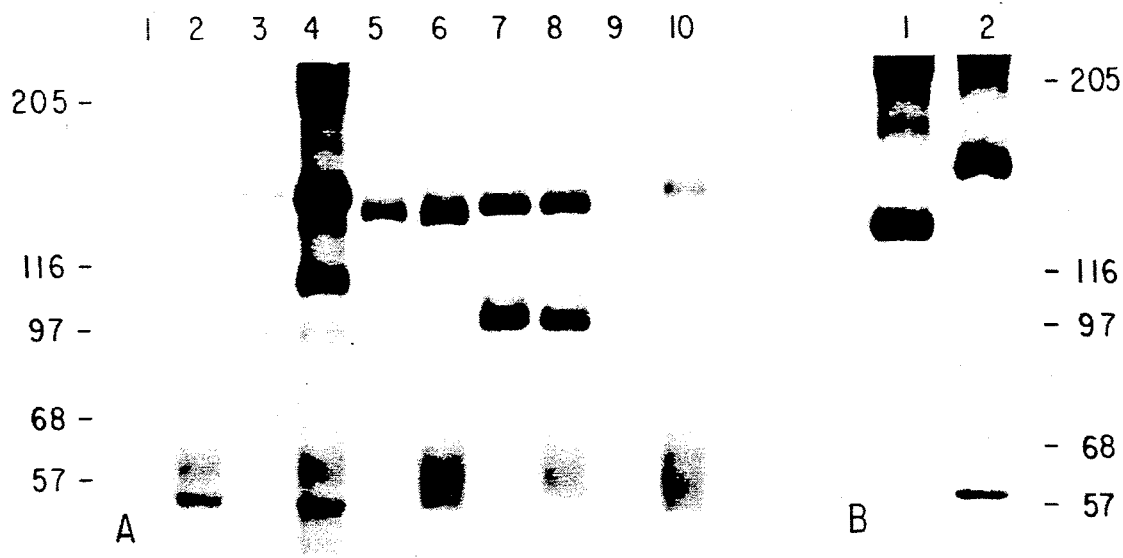
FIG. 9A  FIG. 9B

5,077,216

MONOCLONAL ANTIBODIES SPECIFIC FOR A HUMAN MONONUCLEAR PHAGOCYTE-SPECIFIC ANTIGEN

BACKGROUND OF THE INVENTION

The identification of tumor-associated antigenic markers have been exploited for diagnosis, surveillance and treatment of cancer. The development of monoclonal antibody technology has facilitated the search for phenotypic heterogeneity of tumors and normal tissues and the recognition of tumor-associated antigens. Monoclonal antibodies specific for the tumor-associated antigens can be used as targeting agents for the diagnosis and treatment of cancer. For example, antibodies can be used to detect tumors by means of immunoscintigraphic imaging and to treat tumors by immunotherapy. The lack of sufficient tumor specificity is still a problem. More selective antibodies are necessary to expand the clinician's armamentarium of anti-cancer agents.

SUMMARY OF THE INVENTION

This invention pertains to a human mononuclear phagocyte-specific antigen. The antigen (hereinafter the p155 antigen) is a trypsin-sensitive protein of molecular weight approximately 155 kDa (as determined by gel electrophoresis under reducing conditions). The p155 antigen is expressed on human monocytes, monocyte-derived macrophages and peritoneal macrophages, but is not expressed on human granulocytes, lymphocytes and platelets. In addition, the p155 antigen is not expressed by other human nonphagocytic cell lines. The invention also pertains to monoclonal antibodies specific for the antigen. Because the p155 antigen is associated with phagocyte-specific cells, the antibodies can be used to target phagocytic cells. For example, the antibodies can be used alone, as fragments or as immunotoxins to treat cancers of phagocytic cells such as myeloid leukemia. In addition, the antibodies can be used to produce heteroantibodies for targeting phagocytes to a desired antigen such as a cancer cell.

BRIEF DESCRIPTION OF THE DRAWINGS

FIG. 8 shows the radioimmunoprecipitation using $^{125}$I-labeled monocyte lysates after preclearing with Mac-2-158.

FIG. 9A shows radioimmunoprecipitation of $^{125}$I proteins from lysates of unstimulated and stimulated human monocytes.

FIG. 9B shows the radioimmunoprecipitation of the p155 antigen under non-reducing (1) and reducing (2) conditions.

DETAILED DESCRIPTION OF THE INVENTION

Figure 1:
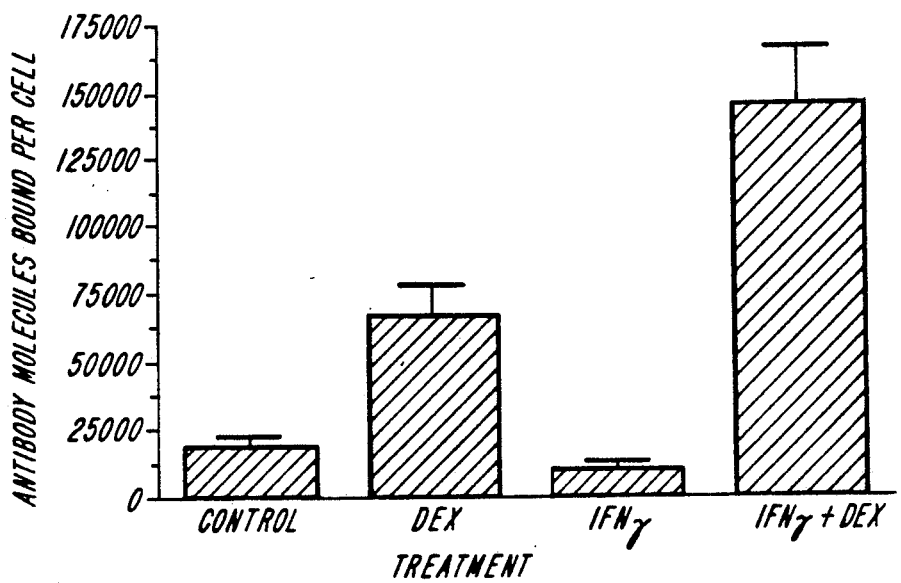
FIG. 1 shows the stimulation of the p155 antigen with dexamethasone (DEX) and rIFN-gamma plus DEX.

The p155 antigen is specific to human phagocytic cells. The antigen is expressed on human monocytes, monocyte-derived macrophages and peritoneal macrophages, but is not expressed on human granulocytes, lymphocytes and platelets. In addition, the antigen is not expressed on other human non-phagocytic cell lines. The p155 antigen is a surface antigen and it is sensitive to trypsin. It has a molecular weight of approximately 155 kDa as determined by polyacrylamide gel electrophoresis under reducing conditions. Because of the antigen's unique association with human phagoctte cells, it can be exploited as a specific marker of these cells which can be used to identify or to target phagocytic cells.

Antibodies which react specifically with the p155 antigen can provide useful therapeutic reagents. For example, monoclonal antibodies which specifically bind to the p155 antigen can be used as targeting molecules to deliver pharmaceutical or cytotoxic agents selectively to phagocytic cells.

Hybridoma cell lines which secrete such monoclonal antibodies can be produced by standard somatic cell fusion techniques. See e.g., Kohler and Milstein, (1975), Nature 256:495-497. Briefly, the procedure is as follows: An animal is immunized with a p155 antigen-containing immunogen preparation. Preferably, the animal is a mouse but other species may be used. The immunogen preparation comprises p155 antigen-bearing cells or cell fragments (such as human monocytes), or a purified or partially purified preparation of the antigen. In a preferred embodiment, an enriched preparation of human monocytes is used as immunogen. The monocytes can be pretreated with interferon and a glucocorticoid (preferably dexamethasone) to increase the numbers of p155 antigen molecules on the cells and to provide more effective immunization. Details of such pretreatment are given in the Exemplification below.

After immunization, antibody-producing cells, (e.g., splenic or peripheral B lymphocytes) are obtained from the animal and fused with an appropriate immortalizing fusion partner, generally a myeloma cell. A preferred fusion partner for fusion with a murine antibody-producing cell is the mouse myeloma NS-1. Fusions can be performed by standard techniques. Hybridomas formed from the fusion process are selected for production of antibody specific for the antigen. This can be accomplished by initially screening for reactivity with monocytes by techniques of cell-staining and flow cytometry and then by further screening for reactivity or lack of reactivity with appropriate cell types.

The monoclonal anti-p155 antibodies of this invention can be used in several different modes of anti-tumor therapy. The antibodies can be used alone either as whole antibodies or as fragments to treat leukemias derived from phagocytic cells such as myeloid leukemia. Generally, whole antibodies are preferred because effector functions mediated by the Fc region are maintained. The antibodies are administered in an amount effective to eliminate the cancerous phagocytic cells. In an alternate form of therapy, the antibodies may be used for extracorporeal treatment of blood or marrow to selectively eliminate phagocytic cancer cells.

The antibodies of this invention may also be used as immunotoxins for the treatment of leukemias derived from phagocytic cells. The immunotoxins comprise antibody coupled to a pharmaceutical or a cytotoxic agent. Various pharmaceutical or cytotoxic agents can be coupled to the antibodies. Examples of useful therapeutic agents include: radioactive compounds (e.g., isotopes of Boron and Rhenium); agents which bind DNA, such as alkylating agents or various antibodies (e.g., daunomycin, adriamycin, chlorambucil); antimetabolites (e.g., methotrexate); and inhibitors of protein synthesis (e.g., diptheria toxin, ricin and toxic plant proteins). The pharmaceutical or cytotoxic agent can be contained within a liposome which is coupled to the antibody.

In the formation of immunotoxins, the whole antibody or an antigen-binding fragment of the antibody can be used. Antibody fragments may be taken up more readily by cells and therefore may have advantages in certain applications.

The pharmaceutical or cytotoxin may be covalently or noncovalently coupled to the antibody. Any conventional technique for such coupling can be used. See, e.g., Buchsbaum, D.J. et al., *Int. J. Rad. Oncol. Biol. Phys.* 13:1701 (198)). Radioisotopes may be attached directly to the antibody or attached via a chelating agent such as DTPA. The immunotoxins of this invention may also be prepared by genetic engineering techniques. For example, DNA sequences encoding an antibody chain can be joined to DNA sequences encoding a protein toxin to provide a contiguous, chimeric molecule.

The immunotoxin is administered to a leukemic patient in amount sufficient to eliminate leukemic, phagocytic blood cells. The immunotoxins of this invention are advantageous because they are directed against a surface molecule which is probably involved in phagocytosis. Because of this, the immunotoxin is likely to be internalized more readily thereby delivering the toxin to the interior of the cell for more effective cytotoxicity. Immunotoxins may also be used for extracorporeal treatment of blood or marrow to selectively eliminate phagocytic cancer cells.

The antibodies of this invention can be used to target phagocytic cells against a desired antigen (e.g. foreign protein, bacterium, virus, or cancer cell). For this purpose bifunctional antibodies such as heteroantibodies can be produced which have the phagocytic specificity and target specificity. The bifunctional antibody can be used to direct a phagocyte to a target. For example, the phagocytespecific antibody of the invention can be coupled to an antibody against a cancer cell. The conjugate can be used to arm a phagocyte such as macrophage (by allowing the heteroantibody to bind the macrophage based upon its phagocyte specificity) and to direct it to the cancer cell (based upon its target antigen specificity).

Expression of the p155 antigen is stimulated by interferons (alpha, beta and gamma types). Stimulation by interferons is dramatic as compared with other cytokines. This response provides a means for determining or monitoring the biological activity of interferons in an individual (for example, an individual who is receiving interferon therapy). Phagocytic cells which bear the p15 antigen can be removed from an individual and examined for the level of p155 antigen expression as indicative of interferon activity. p155 antigen expression can be determined immunochemically, for example, by employing an antibody which binds specifically to the p155 antigen. The antibody can be reacted with cells taken from an individual and binding to the cell surface can be determined (for example, by using a labeled second antibody specific for the anti-p155 antibody) to determine the level of p155 antigen expression by the cells.

The invention is further illustrated by the following exemplification.

EXEMPLIFICATION

Chemical and reagents. All chemicals used were obtained from Sigma Chemical Company, St. Louis, MO unless otherwise indicated. Recombinant IFN-gamma (rIFN-gamma) was the generous gift of Genentech Inc., S. San Francisco, CA.

MAbs. All MAbs used were of murine origin. MAb P3 is an IgG1 which has no known specificity for human leukocytes, and was used to measure nonspecific fluorescence (kindly provided by Dr. Michael W. Fanger, Dartmouth Medical School, Hanover, NH); MAbs 32 and 44 are IgGI MAbs which recognize distinct epitopes on high affinity Fc receptor of IgG (Fc RI) See U.S. Patent Application Serial No. 069,4I2, filed July 1, 1987; IV-3 is an IgG2b which recognizes an epitope on FcRII (kindly provided by Dr. Clark Anderson, Ohio State University, Columbus, OH; See Looney, R. J. et al. (1986) *J. Immunol.* 136:1641; W6/32 is an IgG2a which binds to a framework determinant on HLA-A and -B antigens (Barnstable, C. J. et al., *Cell* 14:9 (1978)); obtained from American Type Culture Collection, Rockville, MD; IVA12 is an IgG2a which binds to a framework determinant on HLA-DR antigens (Shaw et al., (1985) *Hum. Immunol.* 12:192; kindly provided by Dr. D. Capra, University of Texas Southwestern Medical School, Dallas, TX); OKMI is an IgG2b which binds to the iC3b receptor (Sanchez-Madrid, F. et al., (1983) *J. Exp. Med.* 158:1785; Ortho Diagnostic Systems, Inc., Raritan, NJ); anti-leu M5 is an IgG2b which binds to the p150,95 antigen (Lanier, L. L. et al., (1985) *Eur. J. Immunol.* 15:713; Beckton Dickinson, Mountain View, CA); My 7 is an IgG1 which binds to a determinant on human monocytes and granulocytes (Griffin, J.D. et al., (1981) *J. Clin. Invest.* 68:932; kindly provided by Dr. J. Griffin, Dana Farber Cancer Institute, Boston, MA); AML 2-23 and PM-81, IgG2b and IgM MAbs, which recognize different determinants on human monocytes and granulocytes (Ball, E. D. et al., *Proc. Natl. Acad. Sci. USA* 79:5374 (1982)) (kindly provided by Dr. E. D. Ball, Dartmouth Medical School).

Cell Lines. U-937, THP-1, Daudi, HL-60, Molt-4, K-562 and Raji cell lines were obtained from American Type Culture Collection, Rockville, MD. The KG-la cell line was the generous gift of Dr. E. D. Ball. Each cell line was maintained in RPMI 1640 (KC Biological, Lenexa, KS) supplemented with 10% fetal bovine serum (FBS), (Sterile Systems Inc, Logan, UT), 2 mM glutamine, and 50 $\mu$g/ml gentamycin (United States Biochemical Corp., Cleveland, OH) at 37° C. in a humidified atmosphere containing 5% $CO_2$.

Production of hybridomas. Female BALBc mice (Charles River Biological Supply, Wilmington, MA) were immunized intraperitoneally with $20 \times 10^6$ enriched monocytes (see below) that had been treated for 44 hours with 400 international reference units/ml (IRU/ml) of rIFN-gamma plus 200 nM DEX. The cells were washed 3 times in warmed serum-free RPMI 1640 and resuspended in $Ca^{++}$ and $Mg^{++}$ free phosphate-buffered saline (PBS) prior to injection. The mice were re-immunized two weeks later. Five days after the last immunization, splenocytes were fused with NS-1 myeloma cells (kindly provided by Dr. Michael W. Fanger) using standard techniques (See Ball, supra.; Kohler G. and C. Milstein, (1975) Nature(Lond.) 256:495). Hybrid supernatants were screened for their ability to bind to rIFN-gamma plus DEX-treated monocytes by an indirect immunofluoresence assay using a flow cytometer. Hybrids that were initially selected were given a secondary screen against control and monocytes treated with DEX only, rIFN-gamma only, and rIFN-gamma plus DEX. Chosen hybrids were then cloned by limiting dilution and expanded in medium or as ascites. MAb isotype was determined by an immunoblot assay using isotypespecific antisera.

Preparation of leukocytes. Leukocytes used for hybrid screening were separated from heparinized whole venous blood over Ficoll-Hypaque M-85 (Ferrante, A. and Y. H. Thong (1978) J. Immunol. Methods, 24:389). The mononuclear cell (MNC) fraction was washed 5 times in warmed serum-free RPMI 1640 and resuspended at $2 \times 10^6$/ml in monocyte culture medium containing RPMI 1640, 10% pooled human serum, 25 mM hepes (-N-2-HydroxyethylpiperazineN'-2-ethanesulfonic acid), $5 \times 10^{-5}$ M 2-mercaptoethanol, and 50 µg/ml of gentamycin. The granulocyte fraction was washed 3 times in serum-free RPMI 1640, which included a 10 sec hypotonic lysis in distilled water to remove contaminating red blood cells. The hypotonic lysis was quenched by the addition of an equal volume of twice-concentrated PBS. The granulocytes were resuspended in monocyte culture medium at $9 \times 10^5$/ml and both fractions were cultured separately in teflon TM beakers. Half of the monocytes received 400 IRU/ml of rIFN-gamma plus 200 nM DEX, while the other half as well as the granulocyte fraction received no treatment. Incubation was at 37° C. in a humidified atmosphere containing 5% $CO_2$ Cells were harvested and stained with hybrid supernatants 40–44 hours later as described below.

For all other experiments MNCs were obtained from leukapheresis packs of normal donors followed by enrichment for monocytes as previously described (Shen, L. et al., (1986) Clin. Exp. Immunol. 65:387). The enriched monocytes were cultured in monocyte culture medium at $2 \times 10^6$/ml in either teflon TM beakers or 96-well plates. 96-well plates were pre-coated with 50 µl/well of FBS overnight at 37° C. prior to use. After receiving treatments the cells were incubated for the times indicated at 37° C. in a humidified atmosphere containing 5% $CO_2$. Unless otherwise indicated, DEX was used at a concentration of 200 nM, and rIFN-gamma was used at a concentration of 400 IRU/ml.

Staining and flow cytometry. Cells grown in teflon TM beakers were harvested by vigorous pipetting, pelleted at 400×g, and resuspended in ice cold RPMI 1640 containing 2 mg/ml of bovine serum albumin (1640-BSA). For hybrid screening, the monocyte and granulocyte fractions were pooled after harvesting in order to keep the number of samples to a minimum. For analysis of freshly-isolated leukocytes, the mononuclear cells and granulocytes were pooled after washing and resuspended in ice cold 1640-BSA. In all experiments aliquots of cells were added to wells of a 96-well plate on ice and stained with saturating amounts of MAb supernatant in the presence of $4.8 \times 10^{-5}$ M human IgG (I 4506, Sigma Chemical Co., St. Louis, MO) at 4° C. for 2 hours. They were then washed 3 times with cold PBS containing 2 mg/ml BSA (PBS-BSA) and post-stained with saturating amounts of fluorescein isothiocyanateconjugated goat anti-mouse immunoglobulin (FITC-GAM) (Caltag Antibodies Inc., S. San Francisco, CA) for 1 hour at 4° C.. The cells were washed again and fixed in cold 1% paraformaldehyde (Eastman Kodak Co., Rochester, NY). When MNCs were grown in a 96-well plate, the supernatant was removed by a rapid inversion and the cells were stained as above. For cell lines, cells were harvested in log phase and pelleted at 400 x g. They were resuspended in 1640-BSA and stained in 96-well plates as above. Platelets were isolated and stained as described by Lazarchick, J. et al. (1984) Diagnostic Immunol. 2:238.

Cell-associated immunofluorescence was assayed with a Cytofluorograph System 50H and the 2150 computer using a three decade logarithmic amplifier (Ortho Diagnostic Systems, Westwood, MA). For each experiment the instrument was calibrated prior to assay with quantitative fluorescein microbead standards (LeBouteiller, P. et al. (1983) J. Immunol. Methods 61:301) (Flow Cytometry Standards Corp., Research Triangle Park, NC). A standard curve was constructed by plotting FITC molecules per bead versus log of mean fluorescence intensity (MFI). Relative MAb sites per cell, which represent the binding of FITC-GAM per cell, were calculated by dividing the number of FITC molecules per cell by fluorescein to protein ratio of the FITC-GAM. Unless otherwise indicated, relative MAb sites per cell represent specific binding of FITC-GAM, i.e., the binding after subtracting the value of the irrelevant control, MAb P3.

Monocyte surface iodination and immunoprecipitation.

Monocytes grown in teflon TM beakers for 40–44 h with rIFN-gamma plus DEX were harvested and washed 3 times with warmed, serum-free RPMI 1640. $20 \times 10^6$ cells were resuspended in cold PBS and labeled at room temperature with 2.5 mCi of $Na^{125}I$ (Amersham Corp., Arlington Hts, IL) by the lactoperoxidase method according to Manjunath, R. et al. (1986) J. Immunol. 136: 2271. Immediately after iodination the cells were lysed for 30 min on ice in 1 ml of lysis buffer (50 mM Tris base, 0.5% NP-40, 1 mg/ml ovalbumin, 0.14 M NaCl, 1 mM EDTA, 5 µM iodoacetamide, 2 mM phenylmethylsulfonylfluoride, 10 µg/ml aprotinin and 0.02% sodium azide, pH 8.5). Nuclei and debris were pelleted by centrifugation for 5 min at 8000×g. Lysates were precleared with Protein A-Sepharose for 30 min at 4° C.. Aliquots were transferred to polypropylene tubes, quick frozen for 15–20 sec in liquid $N_2$, and stored at −20° C. prior to use.

For immunoprecipitation, lysates were allowed to thaw at 4° C. 10 µl of MAb ascites fluid or 25 µl of purified MAb was added to 100 µl of lysate and the mixture was allowed to incubate overnight at 4° C. The next day the lysates were added to Protein A-Sepharose for 1 hour in the cold. The immunoprecipitates were obtained by pelleting the Protein A-Sepharose by centrifugation for 40 sec at 8000× g, and were washed 4 times in cold wash buffer (lysis buffer plus 0.1% SDS, 0.2% deoxycholate, and 0.5 M NaCl). A final wash was given in wash buffer without NaCl and ovalbumin. When reduced samples only were run on a gel, the immunoprecipitates were resuspended in twice-concentrated sodium docecyl sulfate (SDS) sample buffer containing 5% 2-mercaptoethanol and were boiled for 4 min according to the method of Laemmli, U. (1970) *Nature* (Lond.) 7:680. When reduced and non-reduced samples were run on the same gel, the samples were reduced with sample buffer containing 20 mM dithiothreitol (DTT) and the non-reduced samples received sample buffer containing 5 mM N-ethylmaleimide (NEM), both with boiling for 4 min. After cooling for 1 hour, the reduced samples were capped with a 2.5 molar excess of NEM. High molecular weight standards included in each gel were always run under reducing conditions. Samples were run on 7.5% acrylamide slab gels (Bio-Rad Laboratories, Richmond, CA) prepared according to Laemmli, supra, at 25 mA per gel. Gels were fixed, stained, and dried according to standard procedures. Autoradiograms were done on Kodak X-Omat AR film (Eastman Kodak Co., Rochester NY) using intensifying screens.

Statistical analysis. Groups of data from multidonor experiments were compared by a one-way analysis of variance. If statistical differences existed, multiple comparisons were made by the Neuman-Keuls test. Zar, J. H. *Biostatistical Analysis* (1974) Prentice-Hall, Inc., Englewood Cliffs, NJ, pp. 155. A p value of less than 0.05 was taken to indicate significance.

Results

Monoclonal antibodies (MAbs). 14 hybridomas were selected initially on the basis of strong reactivity to monocytes that had been cultured for 40-44 hours with IFN-gamma plus DEX, plus lack of reactivity to lymphocytes and granulocytes. Five have been characterized. All are of the IgGI isotype. Ascites fluid from each of these MAbs was shown to immunoprecipitate the same radiolabeled protein (p155) (see below). The antibodies have been designated Mac 2-8, 2-38, 2-48, 2-49, and 2-158. Most of the data to be presented was obtained using Mac 2-48 as a representative of this panel, which will be referred to as the p155 MAbs.

Response to rIFN and/or glucocorticoids. The results of the secondary screen are shown in FIG. 1. Human monocytes were cultured for 40-44 hours with medium alone (control), 200 nM DEX, 400 IRU/ml rIFN-gamma, and a combination of rIFN-gamma plus DEX. Cells were stained as outlined above. The results represent the means±SEM of triplicate samples for N=7 donors. DEX vs. control, p<0.01; rIFN-gamma plus DEX vs. control, p<0.001.

Analysis of 7 donors indicated that for Mac 2-48, there were approximately 20,000 relative binding sites per cell on unstimulated monocytes. Reactivity increased approximately 3.5-fold after treatment with 200 nM DEX (p<0.05 versus control). Treatment with rIFN-gamma alone reduced reactivity by more than 50% for 7 donors, and had no effect for 2 donors.

Figure 2:
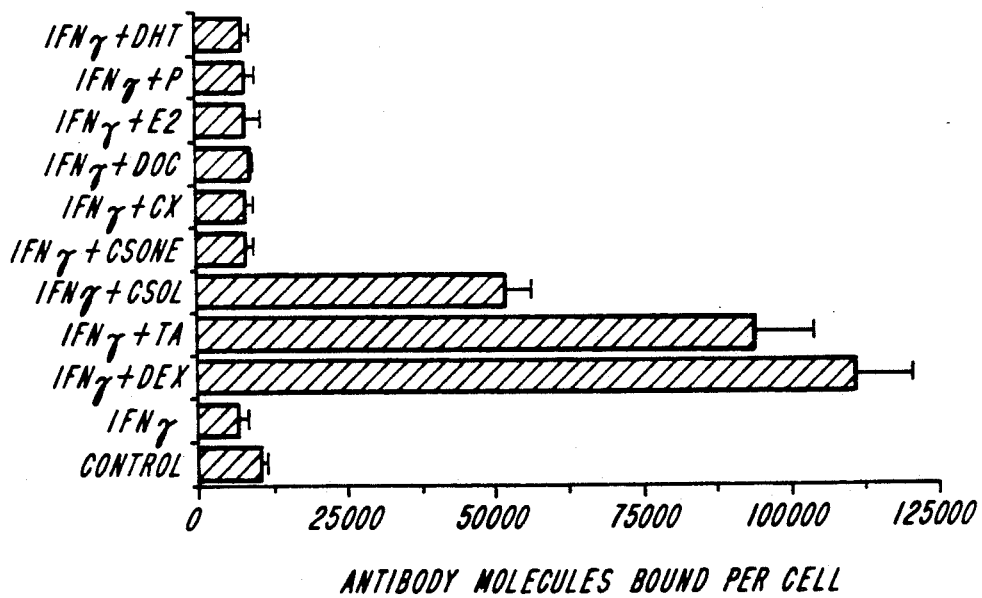
FIG. 2 shows the specificity of rIFN-gamma plus glucocorticoid stimulation of the p155 antigen.

The specificity of the glucocorticoid effect is shown in FIG. 2. Human monocytes were cultured for 40 hours with 400 IRU/ml rIFN-gamma plus 500 nM of various steroids. Cells were stained with Mac 2-48 as outlined in the above. Only for the glucocorticoid hormones cortisol (CSOL), triamcinolone acetonide (TA), and dexamethasone (DEX) was there an increase in the surface binding of Mac 2-48 over unstimulated control cells. DHT, dihydrotestosterone; P, progesterone; E2, estradiol-17; DOC, deoxycorticosterone; CX, cortexolone, CSONE, cortisone.

Figure 2A:
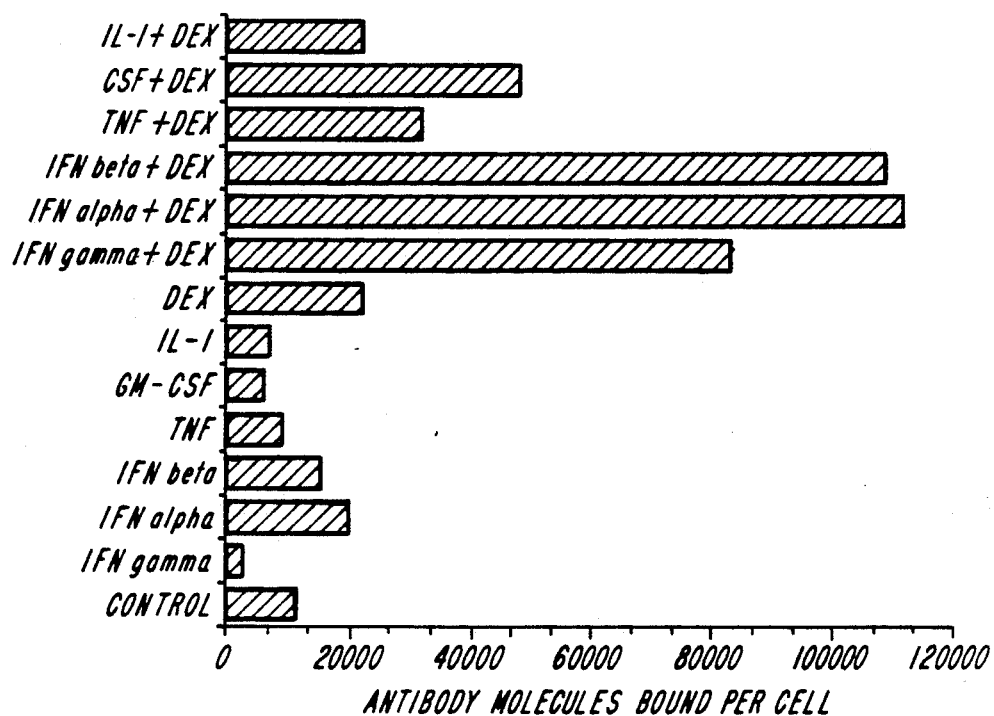
FIG. 2a shows the specificity of cytokine plus glucocorticoid stimulation of the p155 antigen.

The specificity of the interferon response is shown in FIG. 2a. Human monocytes were cultured as above, with 40 IU/ml of rIFN and other cytokines, with and without 200 nM DEX. Cells were stained as outlined above. Enhanced surface binding of Mac 2-48 over unstimulated controls was seen most dramatically with all three rIFNs (-alpha, -beta, and -gamma) in the presence of DEX.

Figure 3:
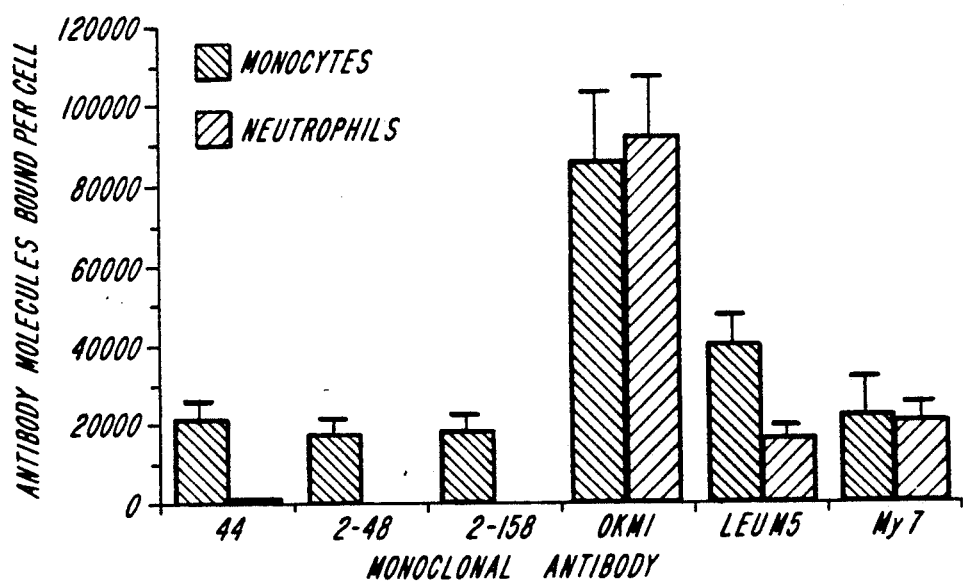
FIG. 3 shows monoclonal antibody staining of freshly isolated human leukocytes.
Figure 4:
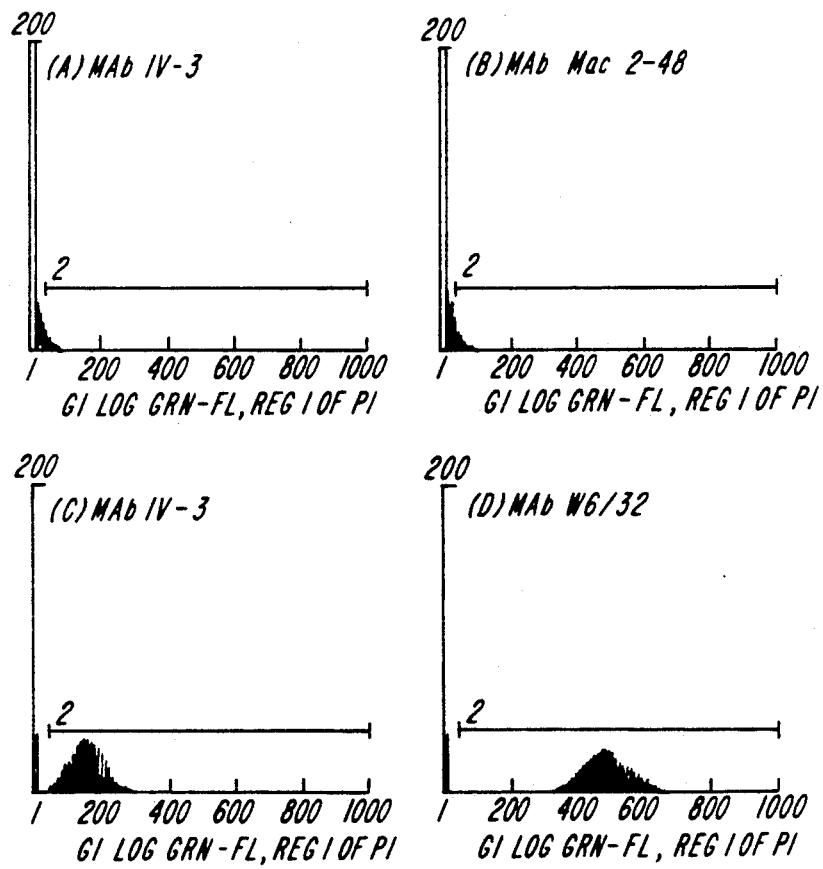
FIG. 4 shows the lack of expression of the p155 antigen on freshly-isolated human platelets.

Reactivity of MAbs to leukocytes and leukocytelike cell lines. In order to compare reactivity of the p155 MAbs with the reactivity of previously defined MAbs, freshly isolated MNCs and granulocytes were studied. Lymphocyte, monocyte and granulocyte subpopulations were delineated according to blue forward and right angle light scatter. FIG. 3 shows the binding of Mac 2-48 and 2-158 in comparison to the binding of MAbs My 7, anti-LEU M5, and OKMI for 5 different donors. Monocytes and granulocytes were isolated, pooled and stained with the indicated MAbs as outlined above. The results represent the means ±SEM of triplicate samples for N=5 donors. The latter three MAbs were chosen for comparison because they were shown previously to immunoprecipitate proteins or components of proteins that are similar to p155 in $M_r$(Sanchez-Madrid, supra.; Lanier, L.L., supra.; Look et al. (1985) *J. Clin. Invest.* 75:569) (see below). The results for MAb 44 are included as a monocyte control. As illustrated in the figure, each Mab bound significantly to monocytes (p<0.01 versus MAb P3). The level of OKMI binding was more than 4 times that of Mac 2-48 and 2-158. For granulocytes, My 7, antiLEU M5, and OKMI reacted significantly, as reported previously (See Griffin, J. D. et al., supra; Talle, M. A. et al. (1983) *Cellular Immunol.* 78:83; Schwarting, R. et al. (1985) *Blood* 65:974). MAb 44 bound to granulocytes slightly more than did the MAb P3 control, but we did not attempt to demonstrate whether or not this difference represented specific, i.e., saturable binding. Of importance is the fact that Mac 2-48 and 2-158 did not bind to granulocytes p 0.05 versus MAb P3). Consistent with the procedure used for hybridoma selection, none of the p155 MAbs bound to lymphocytes (not shown); nor did they bind to freshly-isolated platelets from 2 donors. FIG. 4 shows the platelet reactivity for one donor, where MAbs W6/32 and IV-3 were used as positive controls. Platelets from 2 donors were isolated and stained with P3(A), Mac 2-48(B), IV-3(C), and W6/32(D) according to Lazarchick et al. (1984) *Diagnostic Immunol.* 2:228. 5000 platelets were analyzed by flow cytometry. The histograms show log fluorescence vs. cell number of platelets for 1 donor. Both of those MAbs bound to greater than 90% of platelets, but as shown in panel B, the reactivity of Mac 2-48 was approximately equal to that of the negative control MAb P3. Each of the p155 MAbs were tested and shown to be negative in this experiment (not shown). From these data, the expression of the p155 antigen, like the expression of FclRI, appeared to be monocyte-specific.

MAb reactivity to a variety of leukocyte-like cell lines was also tested. There was no significant binding of the p155 MAbs to unstimulated cells of each of the following cell lines: U-937, THP-1, HL-60, KGla, Molt-4, Daudi, K562, and Raji (not shown); nor was there binding to U-937 or HL-60 cells treated for up to 5 days with dimethylsulfoxide (DMSO) or rIFN-gamma plus vitamin D3 (not shown). However, in three experiments, approximately 30% to 80% of U-937 cells were positive for Mac 2-48 when stimulated for 48-72 hours with rIFN-gamma plus DEX (not shown). rIFN-gamma plus DEX stimulation of granulocytes did not induce expression of the p155 antigen (not shown).

Figure 5A:
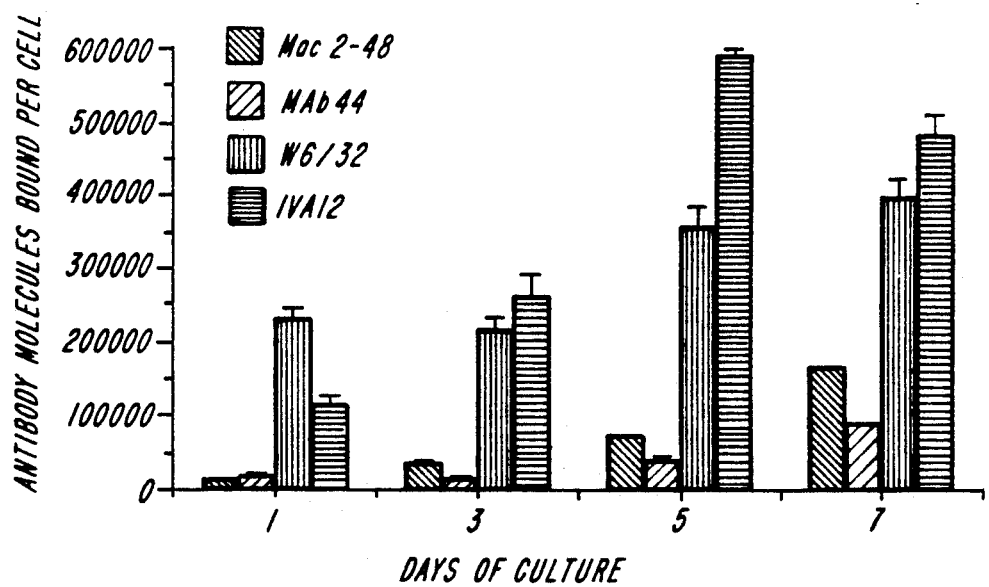
FIG. 5 shows the time course of expression of the p155 antigen on unstimulated (A) and stimulated (B)/human monocytes.
Figure 5B:
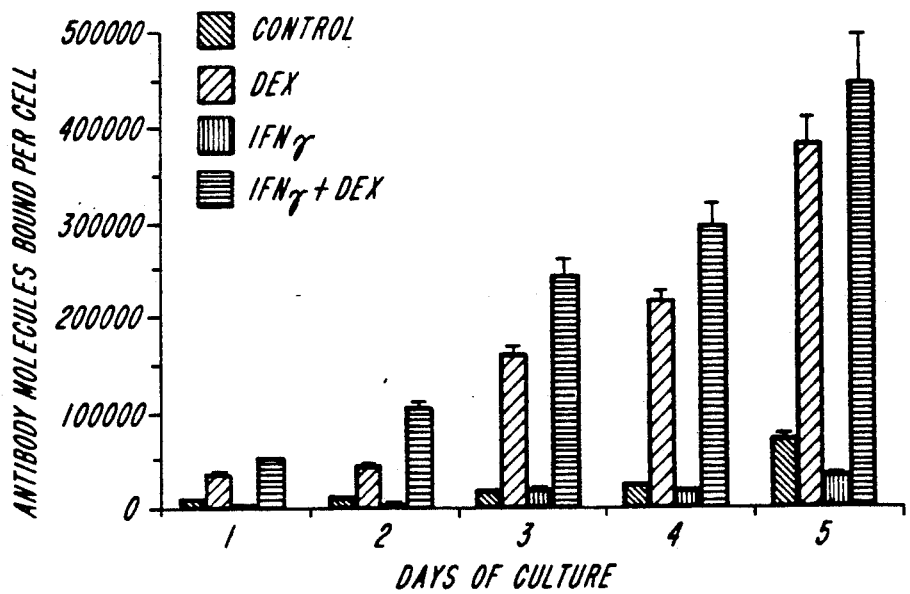

MAb reactivity to monocyte-derived macrophages. Monocytes were cultured and stained over a 7 day period as outlined in above with Mac 2-48, and with Mab 44, W6/32, and IVA12 for comparison. The results in FIG. 5 indicate the Means ±SD of triplicate samples. MAb reactivity to monocytes cultured over a 7 day period is shown in FIG. 5A. Unstimulated monocytes were stained with a variety of MAbs on days 1, 3, 5 and 7. The binding of MAC 2-48 increased with the duration of culture and was highest at day 7. Of the MAbs tested, the increase in binding after 7 days was greatest for Mac 2-48 (13.5 fold greater than the binding at day 1). Although the binding of the other MAbs tested also increased with time of culture, the fold increases after 7 days for each MAb were much smaller that that of Mac 2-48 (Mab 44, 4.7 fold; W6/32, 1.7 fold; IVA12, 4.8 fold). Thus, the increased Mac 2-48 binding is beyond what could be attributed solely to an increase in cell size. This experiment, which was repeated with identical results, suggests that there is constitutive expression of the antigen recognized by Mac 2-48, which is increased during monocyte maturation in vitro. FIG. 5B shows an experiment where monocytes were cultured with continuous exposure to rIFN-gamma and/or DEX for 5 days. The expression of the p155 antigen did not change in response to 400 IRU/ml of rIFN-gamma during days 1-4, and was 50% less than untreated control cells on day 5. For each day expression was augmented by DEX by more than 4-fold, and was maximal in the presence of rIFN-gamma plus DEX. The maximal binding of Mac 2-48 to rIFN-gamma plus DEX-stimulated monocytes at day 7 was quite high, approximately 500,000 relative binding sites per cell. In contrast, the expression of FcRI in response to rIFN-gamma plus DEX was approximately half that of the p155 antigen at day 7 (not shown).

Figure 6:
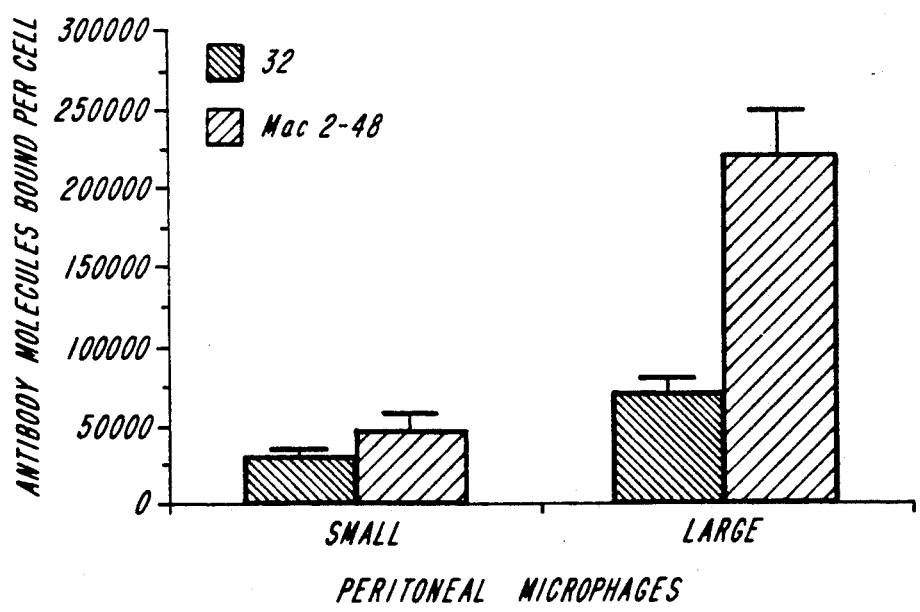
FIG. 6 shows the expression of the p155 antigen on freshly-isolated human peritoneal macrophages.

MAb reactivity to peritoneal macrophages. As an example of the mature macrophage, MAb reactivity to peritoneal macrophages was studied. Peritoneal macrophages were obtained by fluid aspiration during routine diagnostic laparoscopy for infertility. For these experiments subpopulations of macrophages were delineated according to blue forward and right angle light scatter. "Small" macrophages had light scatter values in the same region as that of blood monocytes; "Large" macrophages had higher values for both forward and 90. light scatter. FIG. 6 shows the means +SEM of the binding of MAbs 32 and Mac 2-48 to macrophages from 7 donors. Peritoneal macrophages were isolated, stained with Mac 248 and MAb 32 and analyzed as outlined in the Exemplification. Results represent the mean±SEM of triplicate samples from 7 donors. The binding of Mac 2-48 to small and probably less mature macrophages was not significantly greater than the binding of MAb 32 (46,000±25,000 sites per cell for Mac 2-48 versus 31,000±9000 for MAb 32, p<0.05); however, for large macrophages the binding of Mac 2-48 was significantly greater than the binding of MAb 32 (222,000±65000 sites per cell for Mac 2-48 versus 70,000±25000 for MAb 32, p<0.001).

A summary of MAb reactivity to all of the cells and cell lines that were tested is shown in Table 1.

TABLE 1

SUMMARY OF Mac 2-48 REACTIVITY

| NORMAL CELLS | RELATIVE SITES/CELL | N |
|---|---|---|
| Freshly-prepared human monocytes[1] | ca. 20,000 | 5 |
| Small peritoneal macrophages | ca. 46,000 | 7 |
| Large peritoneal macrophages | ca. 220,000 | 7 |
| Granulocytes[2] | undetectable | 5 |
| Lymphocytes | undetectable | 5 |
| Platelets | undetectable | 2 |
| CELL LINES | | |
| U-937[3,4] | undetectable | 5 |
| THP-1 | undetectable | 3 |
| HL-60[2,4] | undetectable | 3 |
| Daudi[2] | undetectable | 2 |
| Molt-4[2] | undetectable | 2 |
| Raji | undetectable | 1 |
| K562 | undetectable | 2 |
| KG1a | undetectable | 1 |

[1]Expression is strongly enhanced by IFN-gamma + DEX;
[2]No induction by IFN-gamma + DEX;
[3]Inducted by IFN-gamma + DEX;
[4]No induction by either IFN-gamma + Vitamin D$_3$, or DMSO.

Figure 7:
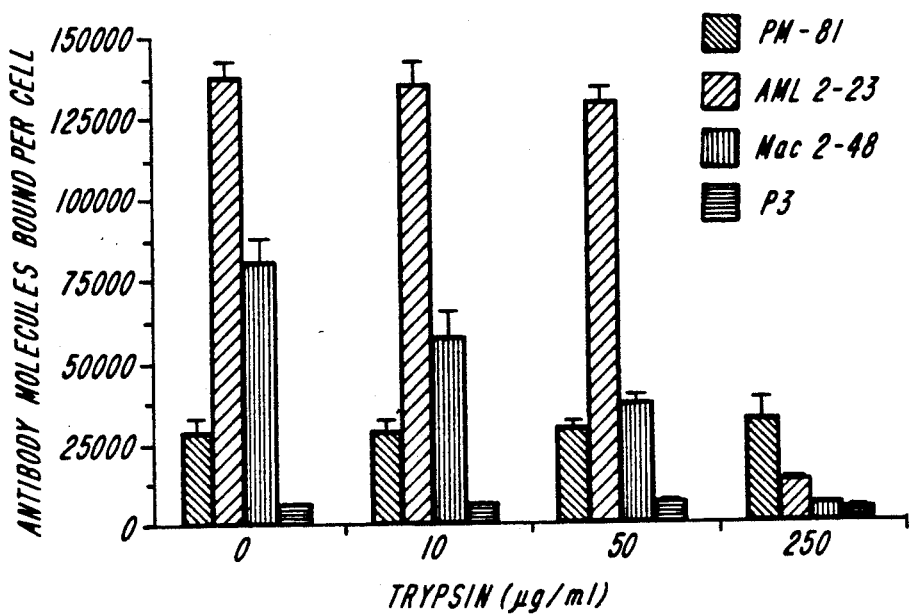
FIG. 7 shows the effect of trypsin on the binding of Mac2-48 to rIFN-gamma plus DEX-treated human monocytes.

Sensitivity to trypsin. In order to further characterize the antigen recognized by the p155 MAbs, the effect of trypsin on the binding of the p155 MAbs was tested. Monocytes were cultured with and without rIFN-gamma plus DEX in FBS-coated 96-well plates for 44 hours. The cells were washed with cold PBS-BSA and treated with varying concentrations of trypsin (Sigma T 8642) for 45 min at 37° C.. The cells were then washed again and stained as in "Methods" with Mac2-48 as well as with PM-81 and AML 2-23 (MAbs which recognize a trypsin insensitive and trypsin sensitive determinant, respectively, Maliszewski, C. R. et al., J. Immunol. 135:1929 (1985)). As shown in FIG. 7, the binding of Mac 2-48 was reduced at all concentrations of trypsin, while the binding of AML 2-23 was significantly decreased only at 250 µg/ml. The reduction for Mac 2-48 was greatest at 250 µg/ml, where its binding was approximately equal to that of MAb P3. This result was also obtained in subsequent experiments with the other p155 MAbs (not shown). These data indicate that the segment(s) containing the MAb-specific epitope(s) of the p155 antigen is cleaved by trypsinization.

Radioimmunoprecipitation. The results of immunoprecipitations using ascites derived from each clone and $^{125}$I labeled rIFN-gamma plus DEX-treated monocyte lysates show that Mac 2-8, 2-38, 2-48, 2-49, and 2-158 immunoprecipitated a dimer of 157 and 115 kilodaltons (kDa) under reducing conditions (see FIG. 8). In order to show directly whether or not these MAbs were binding to the same protein, and whether that protein was different from the ones recognized by MAbs, My 7, anti-LEU M5 or OKMI, a preclearing experiment was done. For this experiment $^{125}$-I labeled rIFN-gamma plus DEX-treated monocyte lysates were immunodepleted of the p155 antigen by three precipitation steps with Mac 2-158 and Protein A-Sepharose. These lysates were then used to test whether or not precipitable protein remained with respect to the p155 Mabs, and Mabs My 7, anti-LEU M5, and OKM1. Precipitated proteins were then resolved by SDS polyacrylamide gel electrophoresis (SDS-PAGE) under reducing conditions (FIG. 8). More than 200,000 CPM were removed by Mac 2-158 after the first preclearing step (lane 1). Approximately 1000 CPM were precipitated by each of the p155 MAbs following depletion with Mac 2-158 (lanes 2-6). The amount of radioactivity corresponding to My 7, anti-LEU M5, and OKM1 was significantly greater than the amount corresponding to the p155 Mabs (lanes 7-9). These results demonstrate that the p155 MAbs each recognize a common protein, and that My7, anti-LEU M5 and OKM1 recognize proteins that are different.

Figure 10:
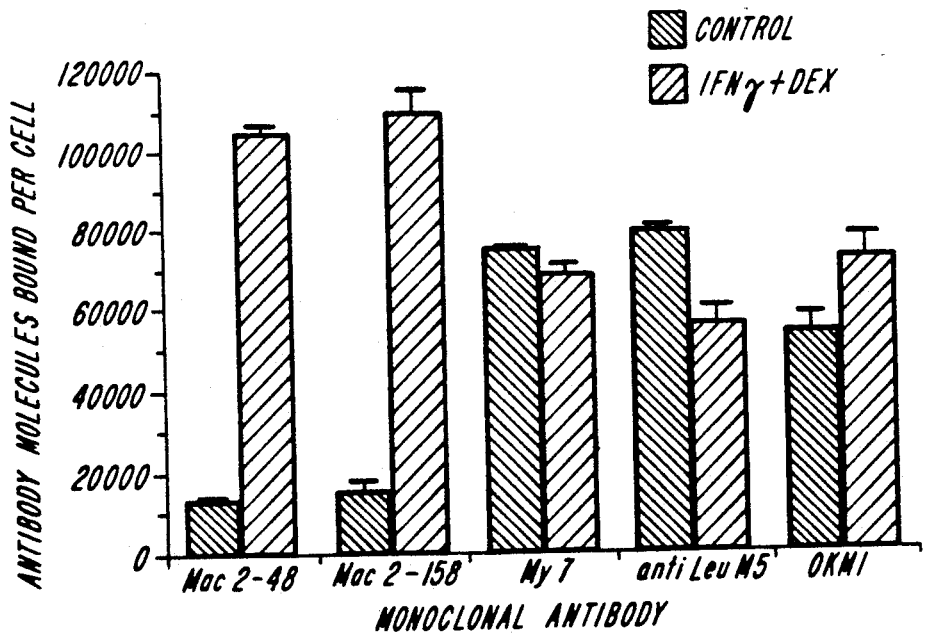
FIG. 10 shows the Mab staining of unstimulated and rIFN-gamma plus DEX-stimulated human monocytes.
Figure 10:
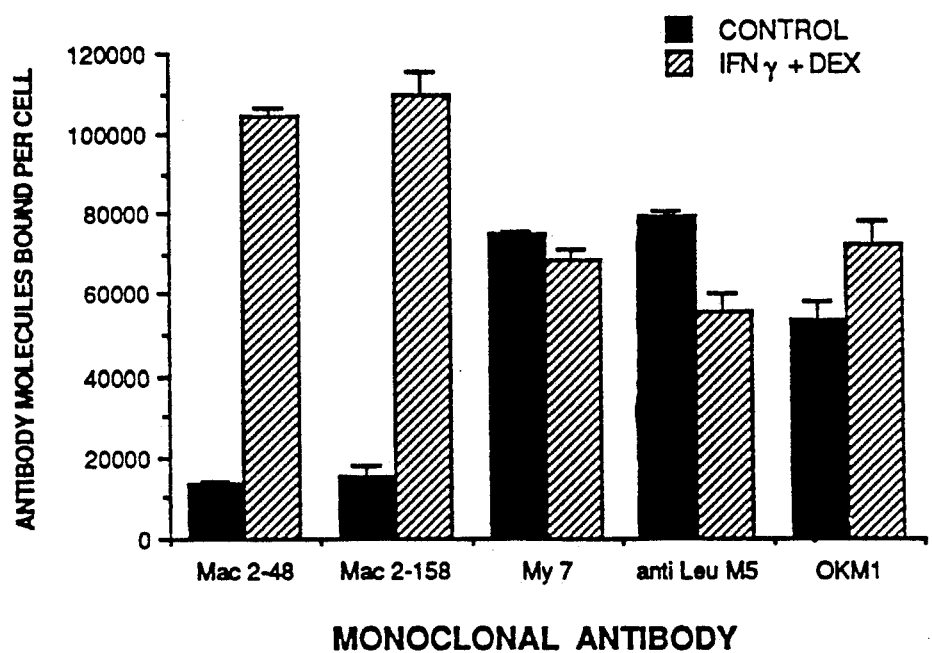

If the p155 MAbs do in fact recognize a surface molecule which occurs at a greater density on rIFN-gamma plus DEX-stimulated monocytes, then more radiolabeled protein should be precipated from lysates of stimulated monocytes relative to lysates of unstimulates monocytes. This is shown in the autoradiogram of FIG. 9A, which includes the results of Mac 2-48 (lanes 1 and 2) with MAbs My 7, anti-LEU M5, and OKM1 (lanes 3-8)- Equivalent sample volumes of immunoprecipitates from radiolabeled unstimulated and rIFN-gamma plus DEX-stimulated monocyte lysates were resolved by SDS-PAGE under reducing conditions. As shown in the autoradiogram, the $M_r$ (in kDa), of the proteins precipitated by each MAb was as follows: Mac 2-47, a dimer of 155, 114; My 7, a monomer of 147; anti-LEU M5, a dimer of 150, 99; OKM1, a dimer of 157,99/Only Mac 2-48 (155,114) precipitated significantly greater radioactivity from lysates of stimulated monocytes than from lysates of monocytes cultured with rIFN-gamma plus DEX (lanes 1 and 2). Similar results were obtained in two different experiments when MAb reactivity of control and stimulated monocytes was determined by immunofluorescence. FIG. 10 shows an experiment where monocytes from one donor were cultured for 72 hours with and without rIFN-gamma plus DEX, prior to staining with Mac 2-48 and 2-158, My 7, anti-LEU M5 and OKM1. The binding of Mac 2-48 and 2-158 on stimulated monocytes was more than 46 times the binding to unstimulated monocytes. For My 7 and anti-LEU M5, the binding was decreased slightly on stimulated monocytes. The binding of OKM1 was slightly increased on stimulated monocytes (1.3-fold greater), a difference far less than that for Mac 2-48 and 2-158.

During this study lysates from 5 different donors were used for immunoprecipitations with Mac 2-48. From 16 experiments, the means ±SD of the larger and smaller Mr bands under reducing conditions were 155±3 and 116±4 kDa respectively. Lysates form three of the donors consistently yielded a dimer while lysates from two yielded only the higher Mr monomer. In order to resolve this discrepancy, immunoprecipitated protein was analyzed under non-reducing as well as reducing conditions. Lysates from four donors were re-tested, and for each lysate, Mac 2-48 precipitated a monomer of $M_r$ 134±2 kDa under non-reducing conditions (not shown). For three of the donors, however, the protein became a dimer under reducing conditions. This suggested that the p155 antigen was being affected by proteolysis in some preparations and that the proteolytic fragments were held together by intrachain disulfide bonds. The addition of 10 g/ml of the protease inhibitors leupeptin, antipain, pepstatin A, and chymostatin to the lysis buffer had no effect on this result when additional lysates from the same donors were re-tested. However, when a cell lysate was made by boiling $^{125}$-I labeled rIFN-gamma plus DEX-treated monocytes for 5 min in normal lysis buffer plus 0.5% SDS, (which was subsequently sequestered by the addition of 2% NP-40) in an attempt to neutralize proteolytic enzymes, Mac 2-48 precipitated a monomer of 133 kDa under non-reducing conditions, and 158 kDa under reducing conditions (FIG. 9B, lanes 1 and 2 respectively). In four previous experiments with the same donor a dimer was present under reducing conditions. From this we conclude that the antigen recognized by the p155 MAbs is probably a monomer, of $M_r$ 155 kDa under reducing conditions, and 134 kDa under non-reducing conditions. The lower molecular weight subunit present under reducing conditions in earlier experiments was most likely an artifact due to a donor-dependent amount of proteolytic activity in those lysates.

DISCUSSION

The monoclonal antibodies (MAbs) of this invention, as represented by Mac 2-8, 2-38, 2-48, 2-49, and 2-158, recognize a trypsin-sensitive protein of $M_r$ 155 kDa (reducing conditions) that appears to be specific to cells of the human mononuclear phagocyte lineage. The p155 antigen is highly expressed on monocytes, monocyte-derived macrophages, and peritoneal macrophages, but is undetectable on human granulocytes, lymphocytes, and platelets, and on numerous cell lines including the monoblastic cell line U-937 and the promyelocytic cell line HL-60. The lack of MAb reactivity to platelets is important for two reasons: 1. It has been shown that platelets and their fragments which adhere to monocytes during isolation can react with platelet-specific MAbs (Breton-Gorius, J. et al., (1987) *Leukemia* 1:131; thus immunofluorescence associated with platelets could be mistaken for the true labeling of monocytes. 2., There are reports of several MAbs which are both platelet and monocytespecific (See Foon, K. A. et al., (1986) *Sem. Hematol.* 23:257).

A review of the literature concerning MAbs which define human myeloid cell antigens revealed none that recognize a monocyte- or macrophagespecific antigen of approximately $M_r$ 155 kDa. There are reports of some, however, which recognize antigens of about 155 kDa which are found on both monocytes and granulocytes. Three of these, MAbs My 7, anti-LEU M5, and OKM1, were chosen for comparison to the MAbs which recognize the p155 antigen. MAb My 7 (Griffin, J.D., supra.; Look, A.T., supra.) binds to a 150 kDa determinant of monocytes and granulocytes, that is present also on U-937 and HL-60 cells. MAb anti-LEU M5 recognizes the p150,95 antigen, which is expressed on monocytes and granulocytes and weakly on U-937 cells (Lanier, L.L., supra.; Schwarting, R. H. et al., (1985) *Blood* 65:974. MAb OKM1 binds to the iC3b receptor of monocytes, granulocytes and null cells and is a dimer of 155 and 95 kDa (Sanchez-Madrid, F.J., supra.; Talle, M.A. et al., (1983) *Cellular Immunol.* 78:83). The latter two MAbs are part of the LFA (Leukocyte Function-Associated Antigen) family that consists of antigens with different alpha subunits non-covalently associated with an identical beta subunit (Sanchez-Madrid supra.; Hynes, R.0., (1987) *Cell* 48:549). It is unlikely that these previously reported MAbs recognize the p155 antigen defined by the p155 MAbs. First, the difference in binding of MAbs My 7, anti-LEU M5, and OKMI to unstimulated versus rIFN-gamma plus DEX-treated monocytes was insignificant when compared to the result using Mac 2-48 and 2-158 (FIG. 10). Second, when the p155 antigen was precleared using Mac 2-158 from lysates of $^{125}$I labeled rIFN-gamma plus DEX-stimulated monocytes, significant amounts of the antigens recognized by MAbs My 7, anti-LEU M5 and OKM1 remained (FIG. 8). A third difference was the inability of the p155 MAbs to bind to cell lines. While MAbs My 7, anti-LEU M5, and OKMI bind to numerous cell lines, including U-937 and HL-60 cells, the p155 Mabs failed to bind to either of these or to other cell lines tested. This also argues against the possibility that MAbs MoU48 (p160-170) (Goyert, S. M. et al., (1986) *J. Immunol.* 137:3909) and U2 (p160) (Takaishi, M. et al., (1985) *J. Immunol.* 135:1523) recognize the p155 antigen, since both MAbs, in addition to binding to granulocytes, bind to U-937, HL-60, and KG1 cells. Therefore, the immunochemical and cell phenotype data strongly suggest that the p155 MAbs recognize a newly-identified antigen specific to the human mononuclear phagocyte lineage.

As shown in FIG. 5A, the expression of the p155 antigen increases as monocytes mature into monocyte-derived macrophages in vitro. The highest level of expression of Mac 2-48 without hormone stimulation was on peritoneal macrophages (Figure 6). Preliminary data by immunocytochemistry indicate that the p155 antigen is associated with macrophages but not other cells in the spleen and liver. Further studies of tissue distribution are currently underway. It appears then that the expression of the p155 antigen may correlate directly to the extent of monocyte maturation, and that this antigen may represent in the least, a phenoclone and I labeled typic marker of mononuclear phagocyte differentiation or maturation. A correlation between the extent of expression of the p155 antigen and a macrophage function such as phagocytosis remains to be investigated.

EQUIVALENTS

Those skilled in the art will recognize, or be able to ascertain using no morethan routine experimentation, many equivalents to the specific embodiments of the invention described herein. Such equivalents are intended to be encompassed by the following claims.

We claim:

1. Monoclonal antibody, or antigen-binding fragment thereof, specific for a human mononuclear phagocyte-specific antigen which is a trypsin sensitive protein of molecular weight 155 kDa as determined by SDS polyacrylamide gel electrophoresis under reducing conditions, which is expressed on human monocytes, monocyte-derived macrophages and peritoneal macrophages, but which is not expressed on human granulocytes, lymphocytes and platelets and which does not bind the p 150,95 alpha subunit on monocytes and macrophages.

2. Monoclonal antibody of claim 1, consisting of Mac 2-48.

3. A hybridoma which secretes an antibody, or antigen-binding fragment thereof, which specifically binds to a human mononuclear phagocyte-specific antigen which is a trypsin sensitive protein of molecular weight 155 kDa as determined by SDS polyacrylamide gel electrophoresis reducing conditions, which is expressed on human monocytes, monocyte-derived macrophages and peritoneal macrophages, but which is not expressed on human granulocytes, lymphocytes and platelets and which does not bind the p 150,95 alpha subunit on monocytes and macrophages.

4. A hybridoma of claim 3, consisting of the Mac 2-48 hybridoma cell line.

* * * * *